United States Patent
Tan et al.

(10) Patent No.: US 7,454,980 B2
(45) Date of Patent: Nov. 25, 2008

(54) ELECTRONIC DEVICE TORSION TESTING

(75) Inventors: Swee Tiong Tan, Singapore (SG); Chung Poh Ong, Singapore (SG); Shang Jiun Wong, Singapore (SG); Kee Ann Chan, Singapore (SG); Cheng Siong Chin, Singapore (SG)

(73) Assignee: Seagate Technology, LLC, Scotts Valley, CA (US)

( * ) Notice: Subject to any disclaimer, the term of this patent is extended or adjusted under 35 U.S.C. 154(b) by 0 days.

(21) Appl. No.: 11/522,763

(22) Filed: Sep. 18, 2006

(65) Prior Publication Data

US 2008/0066556 A1    Mar. 20, 2008

(51) Int. Cl.
*G01N 3/20* (2006.01)
*G01N 3/32* (2006.01)

(52) U.S. Cl. .......................... 73/847; 73/814
(58) Field of Classification Search .............. 73/761, 73/847–854
See application file for complete search history.

(56) References Cited

U.S. PATENT DOCUMENTS

| | | | |
|---|---|---|---|
| 2,030,464 A * | 2/1936 | Nilson | 73/761 |
| 4,858,902 A * | 8/1989 | Hickman | 269/88 |
| 4,866,990 A * | 9/1989 | Peterson et al. | 73/761 |
| 5,184,517 A * | 2/1993 | Kelzer | 73/851 |
| 5,447,072 A * | 9/1995 | Holung | 73/848 |
| 5,546,250 A * | 8/1996 | Diel | 360/97.02 |
| 5,736,646 A | 4/1998 | Dickinson et al. | |
| 5,789,682 A | 8/1998 | Dickinson et al. | |
| 6,067,860 A * | 5/2000 | Grams et al. | 73/814 |
| 6,094,980 A | 8/2000 | Larson et al. | |
| 6,289,743 B1 * | 9/2001 | Norton | 73/847 |

OTHER PUBLICATIONS

"Coupled" Dictionary.com. Acessed Oct. 13, 2007. <http://dictionary.reference.com/search?q=coupled&r=66>.*
"Hard Disk Drive Defintion". Acessed Oct. 13, 2007. <http://www.bellevuelinux.org/hdd.html>.*

* cited by examiner

*Primary Examiner*—Edward Lefkowitz
*Assistant Examiner*—Jonathan Dunlap
(74) *Attorney, Agent, or Firm*—Shumaker & Sieffert P.A.

(57) ABSTRACT

A test device comprises a base and a first fixture coupled to the base. The first fixture holds a first portion of an electronic device mounted in the test device. The test device includes a second fixture rotatably coupled to the base and a lever coupled to the second fixture. The second fixture holds a second portion of the electronic device mounted in the test device. The test device also includes an actuator that forcibly moves the lever to rotate the second fixture and apply a torsion stress on the electronic device mounted in the test device. The test device may be used to test the functionality of electronic devices, such as small form-factor disc drives, while under torsion stresses.

21 Claims, 3 Drawing Sheets

ELECTRONIC DEVICE TORSION TESTING

TECHNICAL FIELD

The invention relates to torsion testing of electronic devices.

BACKGROUND

Many portable consumer devices, such as notebook computers, cell phones, digital music players, personal digital assistants (PDAs) and the like may include a small form factor disc drive for data storage. For example, one currently available small form factor disc drive with a five gigabyte (Gb) capacity has a profile smaller than a credit card with a thickness of less than a quarter inch.

Small form factor disc drives are more susceptible to external shocks and other forces than the larger disc drives commonly designed for use in desktop computers. Portable electronic devices tend to experience significant shocks and forces through normal everyday use. For example, a user may accidentally drop a portable electronic device or a user may place a portable electronic device in a back pants pocket and sit on it. If a disc drive inside the portable electronic device breaks as a result of such external shocks and forces, the portable electronic device itself will likely be unusable. For these and other reasons, small form factor disc drives should be robust enough to withstand the external shocks and forces associated with portable electronic devices.

SUMMARY

In general, the invention is directed to techniques for torsion testing of electronic devices. Torsion testing of an electronic device includes twisting an exterior housing of the electronic device, e.g., twisting under a defined torque or a defined angular displacement and testing the functionality of the electronic device during and/or after twisting. Embodiments of the invention include testing processes and machines for using the processes.

In one embodiment, the invention is directed to a test device comprising a base and a first fixture coupled to the base. The first fixture holds a first portion of an electronic device mounted in the test device. The test device includes a second fixture rotatably coupled to the base and a lever coupled to the second fixture. The second fixture holds a second portion of the electronic device mounted in the test device. The test device also includes an actuator that forcibly moves the lever to rotate the second fixture and apply a torsion stress on the electronic device mounted in the test device.

In another embodiment, the invention is directed to a method comprising incrementally twisting an electronic device according to a plurality of increments. A strain on the electronic device caused by the incremental twisting changes for each of the plurality of increments. The method further comprises testing the electronic device at least some of the plurality of increments to determine functionality of the electronic device during the at least some of the plurality of increments.

In another embodiment, the invention is directed to a method comprising a means for applying a torsion stress to a disc drive, a means for measuring the torsion stress applied to the disc drive and a means for determining the functionality of the disc drive while the torsion stress is applied to the disk disc drive.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
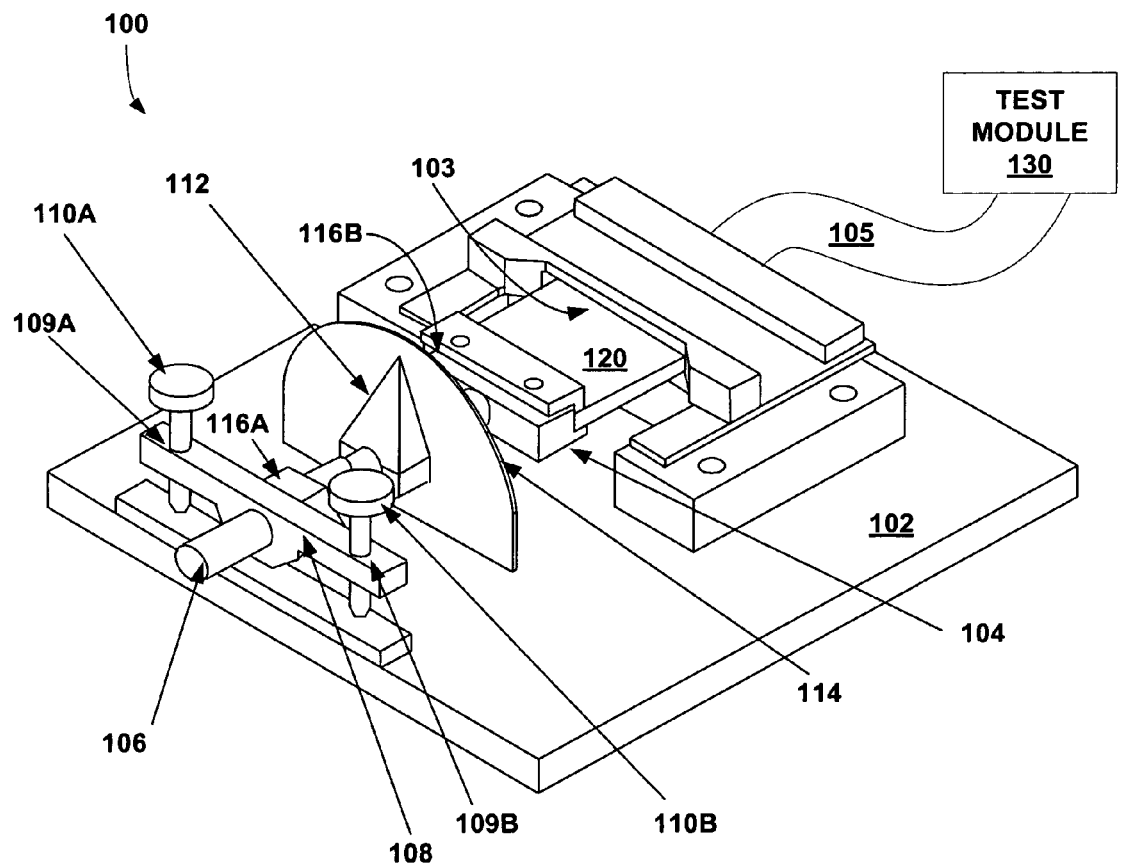
FIG. 1 is an illustration of a torsion testing device that provides torsion testing according to defined angular displacements.

FIG. 1 is an illustration of torsion testing device 100, which allows torsion testing according to defined angular displacements of electronic device 120. Torsion testing device 100 includes clamp 103 that fixedly couples electronic device 120 to base 102. Torsion testing device 100 also includes clamp 104 that rotatably couples the opposite end of electronic device 120 to base 102. Electronic device 120 is supported only by clamps 103 and 104.

Clamp 104 is coupled to shaft 106. Shaft 106 is supported by rotary bearings 116A and 116B to rotatably couple clamp 104 to base 102. Shaft 106 also connects clamp 104 to lever 108. Lever 108 includes two screw holes 109A and 109B (screw holes 109) through which screws 110A and 110B (screws 110) pass through. Screws 110 are actuators that can be extended to press on base 102 to apply a torsion stress to electronic device. E.g., if screw 110A is extended to press on base 102, lever 108, shaft 106 and clamp 104 rotate clockwise (from the viewpoint shown in FIG. 1). The interaction of screws 110 on lever 108 and shaft 106 allows high precision at high loads, which is necessary for accurate testing of electronic device 120. The rotation of lever 108, shaft 106 and clamp 104 is limited to a fixed line defined by bearings 116, which hold shaft 106. Only one of screws 110 is used at a time to apply a torsion stress on electronic device 120.

Pointer 112 is connected to shaft 106 and serves to indicate the angular position of shaft 106 relative to base 102 on protractor 114. Lever 108, shaft 106 and clamp 104 are significantly stiffer than electronic device 120, such that substantially all the relative motion of lever 108 compared to base 102 is experienced by electronic device 120. The relative change in the position of pointer 112 relative to protractor 114 from a neutral position serves as a measurement of the torsion stress on electronic device 120. Using this measurement, electronic device 120 can be twisted to incrementally increase the torsion stress on electronic device 120. For example, shaft 106 may be rotated a total of four degrees in increments of one degree. The functionality of electronic device 120 may be tested at each increment.

As shown in FIG. 1, torsion testing device 100 includes test module 130, which tests the functionality of electronic device 120. Test module 130 is electronically connected to electronic device 120 via cable 105. For example, if electronic device 120 is a disc drive, cable 105 may be an IDE, ATA, SCSI, USB or other interface cable. In different embodiments, test module 130 may communicate with electronic device through other means, such as wireless communication. To test the functionality of electronic device 120, test module 130 may instruct electronic device 120 to perform read and/or write operations. For example, test module 130 may instruct electronic device 120 to perform a random write operation. Test module 130 may repeat testing of electronic device 120 at a plurality of angular displacement increments as indicated by pointer 112 on protractor 114. Test module 130 may repeat testing of electronic device 120 automatically or when instructed by a user. For example, a user may manually adjust the angular displacement of shaft 106

In other embodiments, test module 130 may not be required, e.g., the functionality of electronic device 120 may readily determinable without using test module 130. For example, electronic device 120 may be able to perform self-diagnostics. As another example, a user may attempt to operate electronic device 120 to determine its functionality, e.g., if electronic device 120 is a cell phone, a user may attempt to make a phone call to determine if electronic device 120 is functional. Exemplary techniques for using torsion testing device 100 are described in further detail with respect to FIG. 3.

Figure 2:
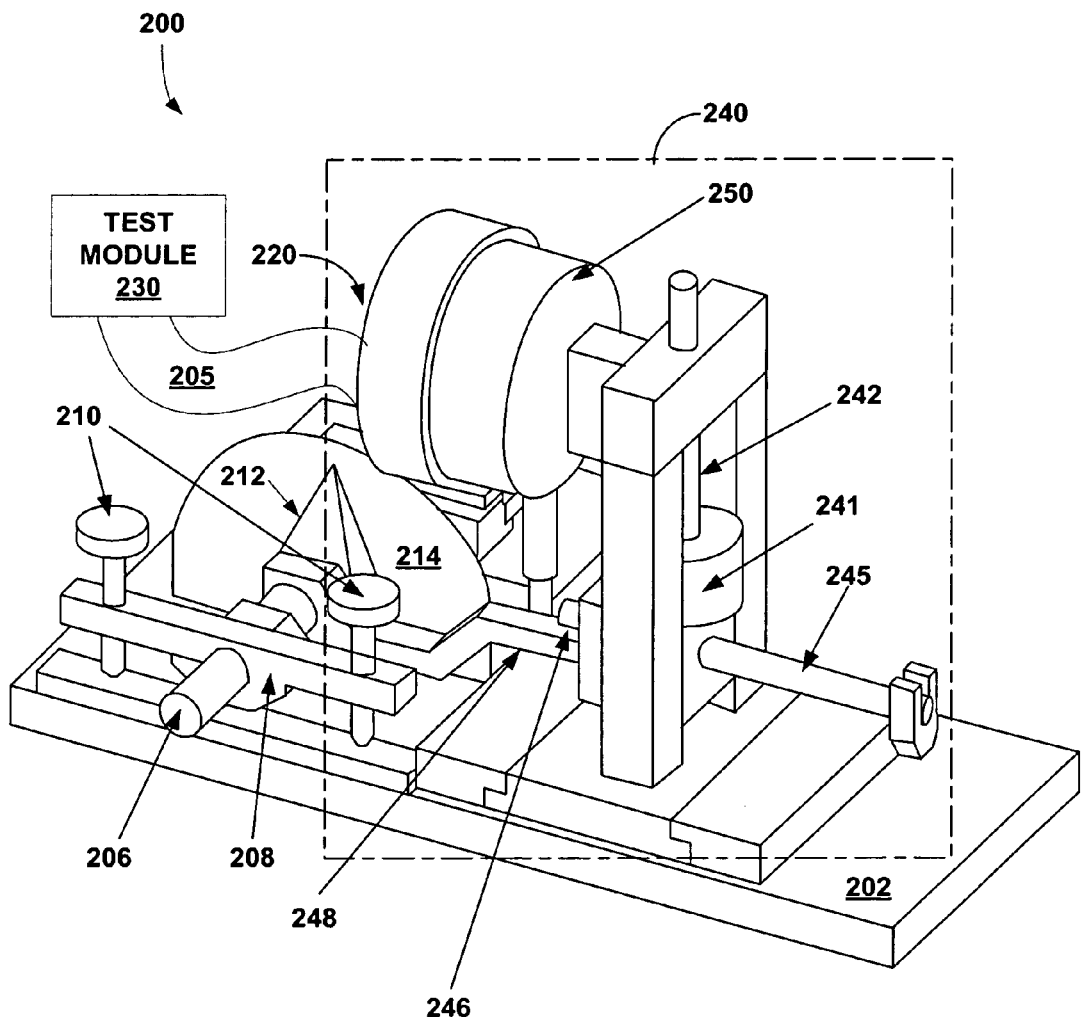
FIG. 2 is an illustration of a torsion testing device that provides torsion testing according to defined angular displacements and/or defined torques.

FIG. 2 is an illustration of torsion testing device 200 providing torsion testing of electronic device 220 according to defined angular displacements and/or defined torques. Torsion testing device 200 is similar to torsion testing device 100 of FIG. 1 with the addition of measurement assembly 240, which is mounted directly on base 202. For example, measurement assembly 240 may be an add-on component for torsion testing device 100 to produce torsion testing device 200. For purposes of brevity, portions of torsion testing device 200 that are the same or similar to torsion testing device 100 are not described in extensive detail.

Electronic device 220 is mounted to torsion testing device 200 with two clamps. The first clamp fixedly couples electronic device 220 to base 202. The second clamp is connected to shaft 206 and rotatably couples the opposite end of electronic device 220 to base 202. Shaft 206 is supported by rotary bearings to rotatably couple shaft 206 to base 202. Lever 208 is also connected to shaft 206. Lever 208 includes two screw holes through which screws 210 pass through. Screws 210 can be extended to press on base 202 and rotate lever 208 a fixed line defined by the rotary bearings that couple shaft 206 to base 202. Screws 210 serve as actuators to forcibly move lever 208 to apply a torsion stress on electronic device 220.

Pointer 212 is connected to shaft 206 and serves to indicate the angular position of shaft 206 relative to base 202 on protractor 214. The relative change in the position of pointer 212 relative to protractor 214 from a neutral position serves as a measurement of the torsion stress on electronic device 220. Using this measurement, electronic device 220 can be twisted to incrementally increase the torsion stress on electronic device 220. The functionality of electronic device 220 may be tested at each increment.

Measurement assembly 240 is fixed to base 202 as part of torsion testing device 200. For example, measurement assembly 240 may be secured to base 202 using screws, clamps or by other means. Measurement assembly 240 includes two measurement instruments useful in determining the stress and strain applied to electronic device 220 by torsion testing device 200: linear displacement gauge 250 and load cell 241. Measurement assembly 240 interacts with shaft 206 via level arm 248, which is fixedly attached to shaft 206. Level arm 248 is sufficiently stiff such that all motion of shaft 206 is transferred directly to level arm 248 and vice-versa.

Linear displacement gauge 250 measures the distance that level arm 248 moves, which allows a calculation of the strain of electronic device 220. The angle of rotation of shaft 206, a measurement of the torsion stress on electronic device 220 can be calculated using Equation 1:

$$\tan^{-1}\left(\frac{\text{level\_arm\_length}}{\text{linear\_displacement}}\right) = \text{angle\_of\_rotation} \quad \text{(Equation 1)}$$

Linear displacement gauge 250 is perpendicular to level arm 248 when torsion testing device 200 holds electronic device 220 in a neutral (unstressed) position. This allows the change in angle of rotation of electronic device 220 to be calculated using an inverse tangent function as demonstrated by Equation 1. Linear displacement gage 250 may provide a much more accurate measurement of the stress on electronic device 220 than pointer 212 and protractor 214. For example, if level arm 248 is 30 centimeters long, a change in measurement of 1 millimeter at linear displacement gauge 250 is equivalent to approximately 0.01 degrees of rotation of shaft 206. This degree of precision is likely not possible with only pointer 212 and protractor 214.

Measurement assembly 240 also includes screw 242, which provides an alternative to screws 210 as a means for applying a torsion stress to shaft 206. It should be noted that linear displacement gauge 250 may be used to measure the angle of rotation of shaft 206 caused by any of screws 210 or screw 242.

Load cell 241 measures the force applied to bar 245 by screw 242. Bar 245, as part of measurement assembly 240, is separate from level arm 248, but directly transfers loads from screw 242 to level arm 248 at interface 246. Bar 245 may be fixedly attached to bar 246 such that screw 242 may be extended or retracted to apply a torsion stress to electronic device 220 either clockwise or counterclockwise respectively. The force measured at load cell 241 may be converted to a torque applied on electronic device 200 according to Equation 2:

cos(angle_of_rotation)*load*load_radius=torque  (Equation 2)

For angles of rotation near zero, Equation 2 can be approximated with Equation 3:

load*load_radius=torque  (Equation 3)

Because of the mechanical advantage provided by lever arm 248, relatively small loads applied by screw 242 can produce large torques on shaft 206. For example, if the load radius is 40 centimeters, a load of 10 kilograms-force produces 3.93 Newton-meters of torque on electronic device 220. This mechanical advantage allows load cell 241 to have a relatively small maximum force measurement capacity.

As shown in FIG. 2, torsion testing device 200 includes test module 230, which is electronically connected to electronic device 220 via cable 205. Test module 230 is operable to test the functionality of electronic device 220. For example, if electronic device 220 is a disc drive, test module 230 may instruct electronic device 220 to perform read and/or write operations. As another example, if electronic device 220 is an electronic device capable of external communications, e.g., a PDA, test module 230 may simply request a response from electronic device 220 to test the functionality of electronic device 220. Test module 230 may repeat testing of electronic device 220 at a plurality of angular displacement increments as indicated by pointer 212 on protractor 214 or by linear displacement gauge 250. In other embodiments, test module 230 may repeat testing of electronic device 220 at a plurality of torque increments as indicated by load cell 241.

In other embodiments, test module 230 may not be required, e.g., the functionality of electronic device 220 may readily determinable without using test module 230. Exemplary techniques for using test device 200 are described in further detail with respect to FIG. 4.

Figure 3:
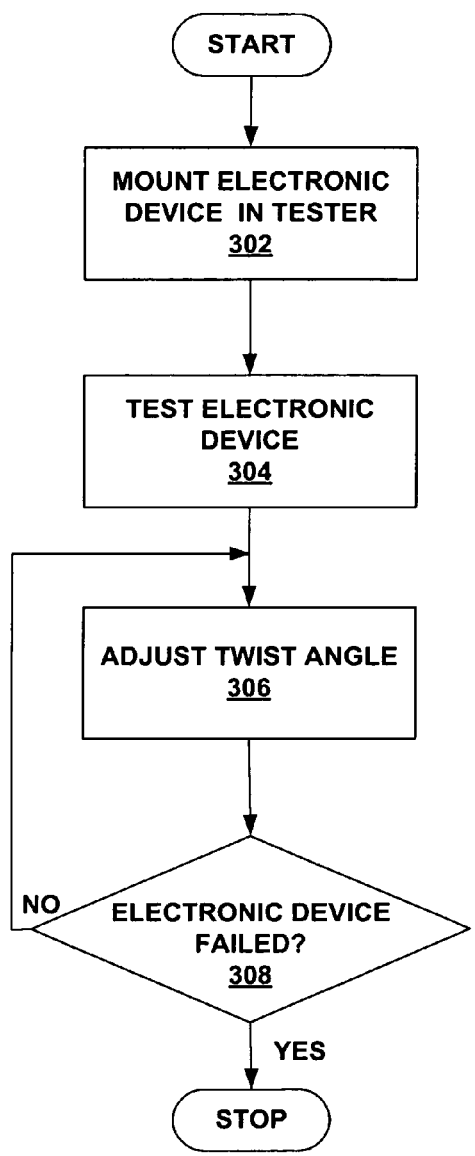
FIG. 3 is a flowchart illustrating techniques for torsion testing an electronic device using incremental angular displacements.

FIG. 3 is a flowchart illustrating techniques for torsion testing an electronic device using incremental angular displacements. For clarity, the techniques shown in FIG. 3 are described with respect to torsion testing device 100 of FIG. 1.

First, electronic device 120 is mounted in torsion testing device 100 (302). Mounting the disc drive in torsion testing device 100 requires securing clamps 103 and 104 and connecting cable 105.

Next, test module 130 tests the functionality of electronic device 120. For example, if electronic device 120 is a disc drive, test module 130 instructs the disc drive to perform a random write operation (304). The random write operation verifies the functionality of the disc drive in an unloaded state. After verifying that electronic device 120 is functional, a user adjusts the twist angle of the disc drive using one of screws 110 (306). For example, the user may increase the twist angle 0.5 degrees as indicated by pointer 112 on protractor 114. After adjusting the twist angle, the user checks to see if electronic device 120 is functional (308). For example, test module 130 retests the functionality of electronic device 120. For example, if electronic device 120 is a disc drive, test module 130 may again instruct the disc drive to perform a random write operation.

If electronic device 120 is not functional the testing of electronic device 120 stops. However, if electronic device 120 is still functional, the user again adjusts the twist angle (306). For example, the user may increase the twist angle another 0.5 degrees as indicated by pointer 112 on protractor 114. After adjusting the twist angle for a second time, the user again checks the functionality of electronic device 120 (308). This process is repeated until electronic device 120 fails. In other embodiments, a user may stop testing after adjusting the twist angle according to a predetermined set of defined angular displacements. While testing of electronic device 120 is generally described as testing whether the drive is function or non-functional, qualitative testing may also be performed. As one example, if electronic device 120 is a disc drive, a bit-error rate test may be performed.

Figure 4:
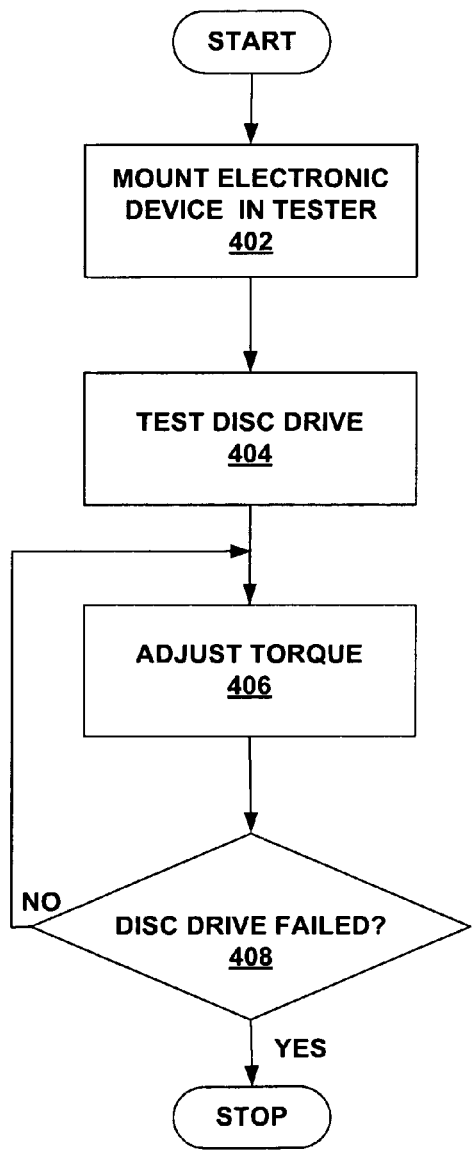
FIG. 4 is a flowchart illustrating techniques for torsion testing an electronic device using incremental torque adjustments.

FIG. 4 is a flowchart illustrating techniques for torsion testing an electronic device using incremental torque adjustments. For clarity, the techniques shown in FIG. 4 are described with respect to torsion testing device 200 of FIG. 2.

First, electronic device 220 is mounted in torsion testing device 200. For the description of FIG. 4, electronic device 220 is described as disc drive (402). However, other electronic devices may also be tested in accordance with the techniques shown in FIG. 4. Mounting the disc drive in torsion testing device 200 requires securing two clamps and connecting cable 205.

Next, test module 230 instructs the disc drive to perform a random write operation (404). The random write operation verifies the functionality of the disc drive in an unloaded state. After verifying that the disc drive is functional, a user adjusts the torque of the disc drive using screw 242 (406). For example, the user may increase the torque 1 Newton-meter as indicated by load cell 241. After adjusting the torque, the user checks to see if the disc drive is functional (408). For example, test module 230 may again instruct the disc drive to perform a random write operation.

If the disc drive is not functional the testing of the disc drive stops. However, if the disc drive is still functional, again adjusts the torque (406). For example, the user may increase the torque another 1 Newton-meter as indicated by load cell 241. After adjusting the torque for a second time, the user again checks the functionality of the disc drive (408). This process is repeated until the disc drive fails. In other embodiments, a user may stop testing after adjusting the torque according to a predetermined set of defined torques. While testing of the disc drive is generally described as testing whether the drive is function or non-functional, qualitative testing may also be performed. As one example, a bit-error rate test or other qualitative test may be performed.

Various embodiments of the invention have been described. For example, embodiments have been generally described with respect to torsion testing that requires manual user operation. However, embodiments of the invention also include automated torsion testing. These and other embodiments are within the scope of the following claims.

The invention claimed is:

1. A test device comprising:
a base;
a first fixture coupled to the base, wherein the first fixture holds a first portion of an electronic device mounted in the test device;
a second fixture rotatably coupled to the base, wherein the second fixture holds a second portion of the electronic device mounted in the test device;
a lever attached to the second fixture; and
an actuator that forcibly moves the lever to rotate the second fixture and apply a torsion stress on the electronic device mounted in the test device.

2. The test device of claim 1, further comprising a shaft that connects the second fixture to the lever.

3. A test device comprising:
a base;
a first fixture coupled to the base, wherein the first fixture holds a first portion of an electronic device mounted in the test device;
a second fixture rotatably coupled to the base, wherein the second fixture holds a second portion of the electronic device mounted in the test device;
a lever coupled to the second fixture; and
an actuator that forcibly moves the lever to rotate the second fixture and apply a torsion stress on the electronic device mounted in the test device, wherein the actuator is a screw.

4. The test device of claim 3, wherein the lever includes a screw hole and the screw passes through the screw hole and presses on the base to move the lever.

5. The test device of claim 4, wherein the screw is a first screw and the screw hole is a first screw hole,
further comprising a second screw,
wherein the lever includes a second screw hole opposite the first screw hole relative to the first screw hole,
wherein the second screw passes through the second screw hole and presses on the base to move the lever in an opposite direction.

6. The test device of claim 1, further comprising at least two rotary bearings that couple the second fixture to the base and limit the motion of the second fixture relative to the first fixture to rotation about a fixed line.

7. The test device of claim 1, wherein the first fixture is a first clamp, and the second fixture is a second clamp.

8. The test device of claim 1, further comprising a load cell that measures a force that creates the torsion stress on the electronic device mounted in the test device.

9. The test device of claim 1, further comprising measurement instrument that provides a measurement that correlates to a relative angle of the second fixture compared to the first fixture.

10. The test device of claim 9, wherein the measurement instrument is a linear displacement gauge.

11. The test device of claim 1, further comprising a test module that communicates with the electronic device to determine functionality of the electronic device while the electronic device is mounted in the test device.

12. The test device of claim 1, wherein the electronic device is a disc drive.

13. A method comprising:
incrementally twisting an electronic device according to a plurality of increments, wherein a strain on the electronic device caused by the incremental twisting changes for each of the plurality of increments;
statically holding the electronic device at each of the plurality of increments; and
while statically holding the electronic device, testing the electronic device at at least some of the plurality of increments to determine functionality of the electronic device during the at least some of the plurality of increments.

14. The method of claim 13, where incrementally twisting the electronic device includes increasing the strain on the electronic device with every increment.

15. The method of claim 14, wherein the method further comprises increasing the strain on the electronic device according to the plurality of increments until the testing determines that the electronic device is not functional.

16. The method of claim 13, wherein the plurality of increments comprise twisting the electronic device according to a set of defined angular displacements.

17. The method of claim 13, wherein the plurality of increments comprise twisting the electronic device according to a set of defined torques.

18. The method of claim 13, wherein the electronic device is a disc drive.

19. The method of claim 18, wherein testing the disc drive includes attempting to read data from the disc drive.

20. The test device of claim 2, further comprising a rotary bearing that supports the shaft to rotatably couple the second fixture to the base.

21. The test device of claim 1, further comprising a test module that communicates with the electronic device to determine functionality of the electronic device while the electronic device is mounted in the test device for each of a plurality of increments,
wherein each of the plurality of increments corresponds to a different static torsion stress applied by the actuator on the electronic device mounted in the test device.

* * * * *